(12) United States Patent
Öhrlein et al.

(10) Patent No.: US 7,199,261 B2
(45) Date of Patent: Apr. 3, 2007

(54) PROCESS FOR THE PREPARATION OF 7-AMINO SYN 3,5-DIHYDROXY HEPTANOIC ACID DERIVATIVES VIA 6-CYANO SYN 3,5-DIHYDROXY HEXANOIC ACID DERIVATIVES

(75) Inventors: Reinhold Öhrlein, Rheinfelden-Herten (DE); Gabriele Baisch, Binzen (DE); Hans Jürg Kirner, Pratteln (CH); Frank Bienewald, Hegenheim (FR); Stephan Burkhardt, Gelterkinden (CH); Martin Studer, Basel (CH)

(73) Assignee: Teva Pharmaceutical Industries Ltd, Petah Tigva (IL)

( * ) Notice: Subject to any disclaimer, the term of this patent is extended or adjusted under 35 U.S.C. 154(b) by 162 days.

(21) Appl. No.: 10/481,704

(22) PCT Filed: Jul. 2, 2002

(86) PCT No.: PCT/EP02/07309

§ 371 (c)(1),
(2), (4) Date: Sep. 10, 2004

(87) PCT Pub. No.: WO03/004456

PCT Pub. Date: Jan. 16, 2003

(65) Prior Publication Data

US 2005/0033086 A1 Feb. 10, 2005

(30) Foreign Application Priority Data

Jul. 6, 2001 (EP) ................... 01810670

(51) Int. Cl.
*C07C 229/00* (2006.01)
(52) U.S. Cl. ................... 560/170
(58) Field of Classification Search ........ None
See application file for complete search history.

(56) References Cited

U.S. PATENT DOCUMENTS 5,599,954 A 2/1997 Mitsuhashi et al.

FOREIGN PATENT DOCUMENTS

| EP | 0385733 A2 | 9/1990 |
| WO | 9307115 A | 4/1993 |
| WO | 09932434 | 7/1999 |

OTHER PUBLICATIONS

J. F. W. McOmie, *Protective Groups in Organic Chemistry*, Plenum Press, London and New York, 1973.
T. W. Greene and P. G. M. Wuts, *Protective Groups in Organic Synthesis*, Third Edition, Wiley, New York 1999.
*The Peptides*, vol. 3 (editors: E. Gross and J. Meienhofer), Academic Press, London and New York, 1981.
Beilstein Database; *Beilstein Institut zur Foerderung der Chemischen Wissenschaften* , Beilstein database No. XP-002199750; [Marie-Pierre Heck, Alain Wagner, and Charles Mioskowski, *Conversion of Primary Amides to Nitriles by Aldehyde-Catalyzed Water Transfer*, J. Org. Chem. 1996, vol. 61, No. 19, pp. 6486-6487].
Beilstein Database; *Beilstein Institut zur Foerderung der Chemischen Wissenschaften* , Beilstein database No. XP-002186065; Beilstein Registry No. 6798562; 4 pages; [Tetrahedron Lett.;EN; 35; 12; 1994; 1999-2002].
Beilstein Database; *Beilstein Institut zur Foerderung der Chemischen Wissenschaften* , database No. XP-002186064; Beilstein Registry No. 1726574; 5 pages.
Beilstein Database; *Beilstein Institut zur Foerderung der Chemischen Wissenschaften* , database No. XP-001038115; [D. W. Brooks, et al., *Remote Substituent Effects in Microbial Reductions of 3-Ketogluarate and 3 Ketoadipate Esters*. Tetrahedron Letters, vol. 25, No. 41, pp. 4623-4626, 1984].
Beilstein Database; *Beilstein Institut zur Foerderung der Chemischen Wissenschaften* , database No. XP-001038113;[R. Roy, et al., *Chemenzymatic Synthesis of A C5-Chiral Building Block: A Substrate Modification Approach*, Tetrahedron Letters, vol. 28, No. 42, pp. 4935-4938, 1987].
Beilstein Database; *Beilstein Institut zur Foerderung der Chemischen Wissenschaften* , database No. XP-000608147; [K. L. Baumann, et al., *The Convergent Synthesis of CI-981, An Optically Active, Highly Posue Selective Inhibitor of HMG-COA Reductase*, Tetrahedron Letters, vol. 33, No. 17, pp. 2283-2284, 1992].
Beilstein Database; *Beilstein Institut zur Foerderung der Chemischen Wissenschaften* , database No. XP-000608146; [P. L. Brower, et al., *The Synthesis of (4r-Cis)-1,1-Dimethylethyl 6-Cyanomethyl-2,2-Dimethyl L-1,3-Dioxane-4-Acetate, A Key Intermediate for the Preparation of CI-981, A Highly Potent, Tissue Selective Inhibitor of HMG-COA Reductase*, Tetrahedron Letters, vol. 33, No. 17, pp. 2279-2282, Apr. 21, 1992].

(Continued)

*Primary Examiner*—Paul A. Zucker
(74) *Attorney, Agent, or Firm*—Kenyon & Kenyon LLP

(57) ABSTRACT

The invention relates to novel synthesis methods for the preparation of the intermediates, which are suitable for the preparation of statin derivatives, especially to novel synthesis methods of the intermediate of formula VI wherein $R_a$ and $R_c$ are each independently of the other hydrogen or a hydroxy-protecting group or together are a bridging hydroxy-protecting group, and $R_b$ is a carboxy-protecting group, which methods are carried out by conversion of the intermediate of formula XIX wherein $R_a$ and $R_c$ are each independently of the other hydrogen or a hydroxy-protecting group, and $R_b$ is a carboxy-protective group

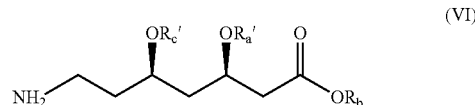

(VI)

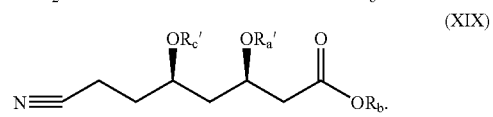

(XIX)

8 Claims, No Drawings

OTHER PUBLICATIONS

U. T. Bornscheuer, R. T. Kazlauskas, Hydrolases in Organic Synthesis, Wiley-VCH, 1999, pp. 61-195, ISBN 3-527-30104-6.

K. Faber, Biotransformation in Organic Chemistry, Springer 1997, Third Edition, pp. 304-306, ISBN 3-540-61688-8.

K. Faber, Biotransformation in Organic Chemistry, Springer 1997, Third Edition, pp. 345-356, ISBN 3-540-61688-8.

H. J. Rehm, G. Reed, Biotechnology, VCH 1998, Second Edition, pp. 40-42.

H. J. Rehm, G. Reed, Biotechnology, VCH 1998, Second Edition, pp. 407-411.

H. -D. Jakubke and H. Jescheit, *Aminosüuren, Peptide, Proteine*, Verlag Chemie, Weinheim, Deerfield Beach, and Basel 1982, Contents and Subject Index.

Jochen Lehmann, *Chemie der Kohlenhydrate: Monosaccharide and Derivate*, Georg Thieme Verlag, Stuttgart 1976, pp. 1-279.

J. F. W. McOmie, *Protective Groups in Organic Chemistry*, Plenum Press, London and New York, 1973.

T. W. Greene and P. G. M. Wuts, *Protective Groups in Organic Synthesis*, Third Edition, Wiley, New York 1999.

*The Peptides*, vol. 3 (editors: E. Gross and J. Meienhofer), Academic Press, London and New York, 1981.

K. Faber, Biotransformation in Organic Chemistry, Springer 1997, Third Edition, p. 305, ISBN 3-540-61688-8.

Beilstein Database; *Beilstein Institut zur Foerderung der Chemischen Wissenschaften*, Beilstein database No. XP-002199750; [Marie-Pierre Heck, Alain Wagner, and Charles Mioskowski, *Conversion of Primary Amides to Nitriles by Aldehyde-Catalyzed Water Transfer*, J. Org. Chem. 1996, vol. 61,. No. 19, pp. 6486-6487].

Beilstein Database; *Beilstein Institut zur Foerderung der Chemischen Wissenschaften*, Beilstein database No. XP-002186065; Beilstein Registry No. 6798562; 4 pages; [Tetrahedron Lett.;EN; 35; 12; 1994; 1999-2002].

Beilstein Database; *Beilstein Institut zur Foerderung der Chemischen Wissenschaften*, database No. XP-002186064; Beilstein Registry No. 1726574; 5 pages; 1957.

Beilstein Database; *Beilstein Institut zur Foerderung der Chemischen Wissenschaften*, database No. XP-001038115; [D. W. Brooks, et al., *Remote Substituent Effects in Microbial Reductions of 3-Ketoglutarate and 3 Ketoadipate Esters*, Tetrahedron Letters, vol. 25, No. 41, pp. 4623-4626, 1984].

Beilstein Database; *Beilstein Institut zur Foerderung der Chemischen Wissenschaften*, database No. XP-001038113;[R. Roy, et al., *Chemenzymatic Synthesis of A C5-Chiral Building Block: A Substrate Modification Approach*, Tetrahedron Letters, vol. 28, No. 42, pp. 4935-4938, 1987].

Beilstein Database; *Beilstein Institut zur Foerderung der Chemischen Wissenschaften*, database No. XP-002217821; 1page 1904.

Beilstein Database; *Beilstein Institut zur Foerderung der Chemischen Wissenschaften*, database No. XP-000608147; [K. L. Baumann, et al., *The Convergent Synthesis of CI-981, An Optically Active, Highly Posue Selective Inhibitor of HMG-COA Reductase*, Tetrahedron Letters, vol. 33, No. 17, pp. 2283-2284, 1992].

Beilstein Database; *Beilstein Institut zur Foerderung der Chemischen Wissenschaften*, database No. XP-000608146; [P. L. Brower, et al., *The Synthesis of (4r-Cis)-1, 1-Dimethylethyl 6-Cyanomethyl-2,2-Dimethyl L-1,3-Dioxane-4-Acetate, A Key Intermediate for the Preparation of CI-981, A Highly Potent, Tissue Selective Inhibitor of HMG-COA Reductase*, Tetrahedron Letters, vol. 33, No. 17, pp. 2279-2282, Apr. 21, 1992].

PROCESS FOR THE PREPARATION OF 7-AMINO SYN 3,5-DIHYDROXY HEPTANOIC ACID DERIVATIVES VIA 6-CYANO SYN 3,5-DIHYDROXY HEXANOIC ACID DERIVATIVES

SUMMARY OF THE INVENTION

The invention relates to novel preparation processes for the preparation of 3,5-dihydroxy-heptanoic acid derivatives and to novel intermediates and processes for their preparation. The dihydroxyheptanoic acid derivatives and the intermediates are suitable for advantageous syntheses of statins.

BACKGROUND OF THE INVENTION

Statins are a class of pharmaceuticals that inhibit the enzyme hydroxymethylglutaryl CoA reductase (HMG-CoA-R) and are therefore widely used as hypolipidaemic agents and agents that lower the level of cholesterol in the blood (hypocholesterollipidaemic agents). All synthetically prepared HMG-CoA-R inhibitors have, as common structural features, an aromatic base structure and the so-called statin side chain, as symbolised by the following formula:

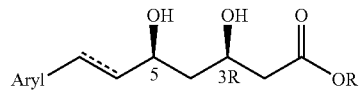

(wherein Aryl denotes aromatic, heterocyclic or aromatic-heterocyclic, unsubstituted or substituted, mono-, di- or poly-cyclic ring systems). Such a structural unit can be found in a whole range of pharmaceutically active agents, such as cerivastatin (Bayer AG), fluvastatin (Novartis), itavastatin (NK-104; Kowa Company Ltd.), BMY 22089 (Bristol-Myers Squibb), rosuvastatin (S-4522, AstraZeneca/Shionogi), glenvastin (Hoechst(Aventis) and atorvastatin (Warner-Lambert/Gödecke-Parke Davies/Pfizer).

The aim of the present invention is to provide new efficient methods of synthesising some known statin derivatives and to provide new intermediate compounds.

GENERAL DESCRIPTION OF THE INVENTION

Key steps in the synthesis according to the invention are early introduction of the correct absolute stereochemistry at C-3 (R) and subsequent regioselective chain lengthening. Unlike the linear synthesis processes in the prior art, the use of the novel statin side chain building blocks allows a convergent synthesis. The invention relates also to novel intermediates.

DETAILED DESCRIPTION OF THE INVENTION

The present invention concerns a process for the preparation of the intermediate of formula VI

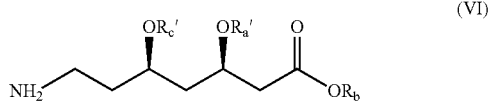

wherein $R_a'$ and $R_c'$ are each independently of the other hydrogen or a hydroxy-protecting group or together are a bridging hydroxy-protecting group, and $R_b$ is a carboxy-protecting group, which is suitable for the preparation of statin derivatives, which process is carried out by conversion of the intermediate of formula XIX

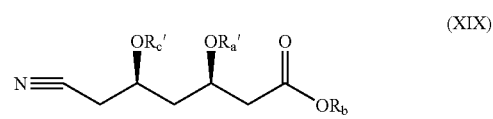

wherein $R_a'$ and $R_c'$ are each independently of the other hydrogen or a hydroxy-protecting group, and $R_b$ is a carboxy-protecting group; wherein compound of formula XIX is prepared by a process which comprises the preparation of a compound of formula I

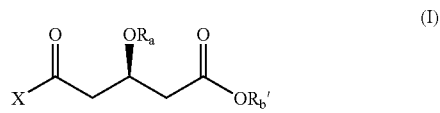

wherein X is halogen, acyloxy, activated hydrocarbyloxy, activated hydrocarbylthio or —N(CH$_3$)—OCH$_3$, $R_a$ is a hydrogen or hydroxy-protecting group and $R_b$ is a carboxy-protecting group, which is converted into an amide of formula I*

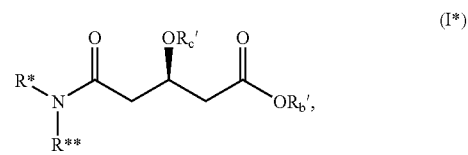

wherein $R_c'$ is hydrogen or a hydroxy-protecting group, $R_b'$ is hydrogen or a carboxy-protecting group and R* and R** are each independently of the other hydrogen or an amide-protecting group, preferably alkyl or substituted alkyl, more preferably $C_1$–$C_4$alkyl, such as methyl, ethyl, n-propyl, iso-propyl, n-butyl, tert-butyl, sec.-butyl, or substituted alkyl, such as benzyl, most preferably benzyl, which compound can then be converted for the preparation of statin precursors, especially those of formula VI already described above:

The conversion of compound of formula I*, wherein R* and R** are each hydrogen, $R_b'$ is a carboxy-protecting group and $R_c'$ is a hydroxy-protecting group is dehydrated to form a nitrile of formula XVII

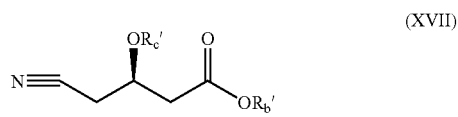

wherein $R_c'$ is a hydroxy-protecting group and $R_b'$ is a carboxy-protecting group; that compound, after removal of the hydroxy-protecting group $R_c'$, is converted by means of a compound of formula XX

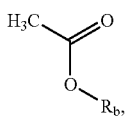

wherein $R_b$ is a carboxy-protecting group in the presence of a strong base, into a nitrile of formula XVIII

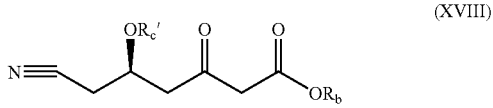

wherein $R_c'$ is a hydroxy-protecting group or, after removal thereof, hydrogen and $R_b$ is a carboxy-protecting group; the compound of formula XVIII wherein $R_c'$ is hydrogen is in turn then converted by diastereoselective reduction into a syn-diol compound of formula XIX

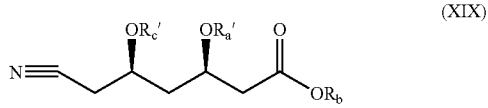

wherein $R_a'$ and $R_c'$ are hydrogen; or, after subsequent introduction of protecting groups, $R_a'$ and $R_c'$ are each independently of the other hydrogen or a hydroxy-protecting group, with the proviso that at least one of the two radicals is such a protecting group, or $R_a'$ and $R_c'$ together are a bridging hydroxy-protecting group; and $R_b$ is a carboxy-protecting group; and by reduction of the cyano function in that compound there is obtained an amino compound of formula VI described above wherein $R_a'$ and $R_c'$ are each independently of the other hydrogen or a hydroxy-protecting group or together are a bridging hydroxy-protecting group, and $R_b$ is a carboxy-protecting group.

The invention relates also to a process for the preparation of the compound of formula I as defined above.

For that purpose, a compound of formula XI

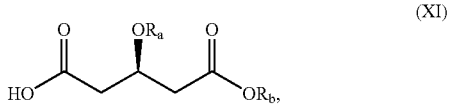

wherein $R_a$ is a hydroxy-protecting group (or, less preferred because the ee is then lower, hydrogen) and $R_b$ is a carboxy-protecting group, is converted into the corresponding compound of formula I using a reagent that introduces the radical X.

The compound of formula XI is in turn advantageously prepared by hydrolysing a compound of formula XII

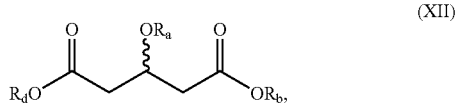

wherein $R_a$ is a hydroxy-protecting group (or, less preferred because the ee is then lower, hydrogen), $R_b$ is a carboxy-protecting group and $R_d$ is hydrocarbyl, by means of an enantio-selective catalyst (preferably by hydrolysis using a biocatalyst) with removal of the radical $R_d$, the corresponding compound of formula XI being obtained directly.

The compound of formula XII is advantageously obtained by reacting a glutaric acid derivative of formula XIII

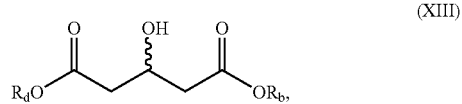

wherein $R_b$ and $R_d$ are as defined for compounds of formula XII, by introduction of a hydroxy-protecting group using the corresponding reagent suitable for the introduction of the protecting group.

The invention relates also to new individual steps of the processes described above, to new combinations of individual steps and to new intermediate compounds.

Unless indicated to the contrary, the general terms (including the reactions and reaction conditions) used hereinabove and hereinbelow preferably have the following meanings—these specific definitions and descriptions of reactions can be used independently of one another instead of the general terms mentioned hereinabove and hereinbelow, resulting in preferred embodiments of the invention:

The prefix "-lower" or "lower" indicates that the radical in question contains preferably up to 7 carbon atoms, especially up to 4 carbon atoms. Lower alkyl is therefore preferably $C_1$–$C_7$alkyl, especially $C_1$–$C_4$alkyl, and may be unbranched or branched one or more times, insofar as possible. Unsaturated radicals, such as alkenyl or alkynyl, have at least two carbon atoms, preferably from 2 to 7, especially from 3 to 7, more especially 3 or 4.

In the processes mentioned hereinabove and hereinbelow, it is possible at any stage, even where not explicitly mentioned, for one or more or all of the protecting groups present in the compounds of formulae I to XIX in question to be removed or for one or more or all of the functional groups that are not to participate in the reaction, or that would interfere with the reaction, to be converted into protected groups by the introduction of suitable protecting groups (especially hydroxy-protecting groups and/or carboxy-protecting groups).

The protection of functional groups by such protecting groups, suitable reagents for their introduction, suitable protecting groups and reactions for their removal will be familiar to the person skilled in the art. Examples of suitable protecting groups can be found in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, N.Y. 1999, in "The Peptidese"; Volume 3 (editors: E. Gross and J. Melenhofer), Academic Press, London and New York 1981, in "Methoden der organischen Chemie", Houben-Weyl, $4^{th}$ edition, Vol. 15/I, Georg Thieme Verlag, Stuttgart 1974, in H.-D. Jakubke and H. Jescheit, "Aminosäuren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974.

Suitable hydroxy-protecting groups are especially selected from those of the acyl or ester type, e.g. lower alkanoyl, such as formyl, acetyl or isobutyroyl, benzoylformyl, chloroacetyl, dichloroacetyl, trichloroacetyl, trifluoroacetyl, methoxyacetyl, phenoxyacetyl, phenylacetyl, p-phenylacetyl, diphenylacetyl, 2,6dichloro-4-methylphenoxyacetyl, 2,6-dichloro-4-(1,1,3,3-tetramethylbutyl)phenoxyacetyl, 2,4-bis(1,1-dimethylpropyl)phenoxyacetyl, chlorodiphenyl-acetyl, 3-phenylpropionyl, 4-azidobutyroyl, 4-methylthiomethoxybutyroyl, (E)-2-methyl-2-butenoyl, 4-nitro-4-methylpentanoyl, 4-pentenoyl, 4-oxopentanoyl, 4,4-(ethylenedithio)-pentanoyl, 5-[3-bis(4-methoxyphenyl) hydroxymethylphenoxy)laevulinyl, pivaloyl, crotonoyl, monosuccinoyl, benzoyl, p-phenylbenzoyl, 2,4,6-trimethylbenzoyl, 2-(methylthiomethoxy-methyl)benzoyl, 2-(chloroacetoxymethyl)benzoyl, 2-[(2-chloroacetoxy)ethyl]benzoyl, 2-[(2-benzyloxy)ethyl]benzoyl, 2-[2-(4-methoxybenzyloxy) ethyl]benzoyl, 2-iodobenzoyl, o-(di-bromomethyl)benzoyl, o-(methoxycarbonyl)benzoyl, 2-chlorobenzoyl, 4-bromobenzoyl, 4-nitrobenzoyl, alkoxycarbonyl, such as methoxycarbonyl, ethoxycarbonyl, isobutoxycarbonyl, methoxymethylcarbonyl, 9-fluorenylmethoxycarbonyl, 2,2,2-trichloroethoxycarbonyl, 1,1-dimethyl-2,2,2-trichloroethoxycarbonyl, 2-(trimethylsilyl)ethoxycarbonyl, 2-(phenylsulfonyl)-ethoxycarbonyl, 2-(triphenylphosphonio)ethoxycarbonyl, vinyloxycarbonyl, allyloxycarbonyl, p-nitrophenoxycarbonyl, benzyloxycarbonyl, p-methoxybenzyloxycarbonyl, 3,4-dimethoxy-benzyloxycarbonyl, o-nitrobenzyloxycarbonyl, p-nitrobenzyloxycarbonyl, dansylethoxy-carbonyl, 2-(4-nitrophenyl)ethoxycarbonyl, 2-(2, 4-dinitrophenyl)ethoxycarbonyl, 2-cyano-1-phenylethoxycarbonyl, S-benzylthiocarbonyl, 4-ethoxy-1-naphthyloxycarbonyl, 3',5'-dimethoxybenzoinyloxycarbonyl, 2-methylthiomethoxyethoxycarbonyl, N-phenylcarbamoyl, dimethylethylphosphinothiolyl, methyldithiocarbonyl; N,N, N',N'-tetramethylphosphoro-diamidoyl, sulfonyl, methanesulfonyl, benzenesulfonyl, toluenesulfonyl, 2-[(4-nitrophenyl)-ethyl]sulfonyl, allylsulfonyl, 2-formylbenzenesulfonyl, nitroxy, or protecting groups of the ether type, such as methyl, substituted methyl, preferably lower alkoxymethyl, especially methoxymethyl (MOM), methylthiomethyl, (phenyldimethylsilyl)methoxymethyl, benzyloxy-methyl, p-methoxybenzyloxymethyl, p-nitrobenzyloxymethyl, guaiacolmethyl, tert-butoxy-methyl, 4-pentenyloxymethyl, silyloxymethyl, lower alkoxy-lower alkoxymethyl, especially 2-methoxyethoxymethyl (MEM), 2,2,2-trichloroethoxymethyl, 2-(trimethylsilyl)-ethoxymethyl or menthoxymethyl, tetrahydropyranyl, 3-bromotetrahydropyranyl, tetrahydrothiopyranyl, 4-methoxythiopyranyl, 1-methoxycyclohexyl, 4-methoxytetrahydrothiopyranyl, S,S-dioxy-4-methoxytetrahydrothiopyranyl, 1-[(2chloro-4-methyl)phenyl]-4methoxypiperidin-4-yl, 1-(2-fluorophenyl)-4-methoxypiperidin-4-yl, 1,4-dioxan-2-yl, tetrahydrofuranyl, tetrahydrothio-furanyl, 2,3,3a,4,5,6,7,7a-octahydro-7,8,8-trimethyl-4,7-methanobenzofuran-2-yl; substituted ethyl, such as 1-ethoxyethyl, 1-(2-chloroethoxy)ethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 2-trimethylsilylethyl, 2-(benzylthio)ethyl, 2-(phenylselenyl)ethyl, tert-butyl; allyl or propargyl, substituted phenyl ethers, such as p-chlorophenyl, p-methoxyphenyl, p-nitrophenyl, 2,4-dinitrophenyl or 2,3,5,6-tetrafluoro-4-(trifluoromethyl)-phenyl, benzyl, substituted benzyl, such as p-methoxybenzyl, 3,4-dimethoxybenzyl, o-nitrobenzyl, p-nitrobenzyl, p-halobenzyl, e.g. p-bromobenzyl, 2,6-dichlorobenzyl, p-cyano-benzyl, p-phenylbenzyl, 2,6-difluorobenzyl, p-azidobenzyl, 4-azido-3-chlorobenzyl, 2trifluoromethylbenzyl or p-(methylsulfinyl)benzyl, 2- or 4-picolyl, 3-methyl-2-picolyl, 2quinolinylmethyl, 1-pyrenylmethyl, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl) phenylmethyl, tri(p-methoxyphenyl)methyl, 4-(4'-bromophenacyloxy)phenyl-diphenylmethyl, 4,4',4''-tris(4,5-dichlorophthalimidophenyl)methyl), 4,4',4''-tris (laevulinoyl-oxyphenyl)methyl, 4,4',4''-tris (benzoyloxyphenyl)methyl, 4,4'-dimethoxy-3''-[N-(imidazolyl-methyl)]trityl, 4,4'-dimethoxy-3''-[N-(imidazolylethyl)carbamoyl], 1,1-bis(4-methoxy-phenyl)-1'-pyrenylmethyl, 4-(17-tetrahydrobenzo[a,c,g,i] fluorenylmethyl)-4',4''-dimethoxytrityl, 9-anthryl, 9-(9-phenyl)xanthenyl, 9-(9-phenyl-10-oxo)anthryl, 1,3-benzodithiolan-2-yl, S,S-dioxo-benzoisothiazolyl; of the silyl ether type, such as tri-lower alkylsilyl, e.g. trimethylsilyl, triethylsilyl, triisopropylsilyl, dimethylisopropylsilyl, diethylisopropylsilyl, dimethylthexylsilyl, tert-butyldimethylsilyl or di-tert-butylmethylsilyl, tert-butyldiphenylsilyl, triphenylsilyl, diphenylmethylsilyl, tris(trimethylsilyl)silyl, (2-hydroxystyryl)dimethylsilyl, (2-hydroxystyryl)-diisopropylsilyl, tert-butylmethoxyphenylsilyl or tert-butoxydiphenylsilyl.

Bridging protecting groups can likewise be used where a molecule contains two hydroxy groups (for example bridging hydroxy-protecting groups formed by $R_a$ and $R_c$ or $R_a'$ and $R_c'$ together) or a hydroxy-protecting group and a carboxy group (for example bridging protecting groups formed by $R_a$ and $R_b$ or $R_a'$ and $R_b$ in the molecules of the corresponding formulae mentioned hereinabove and hereinbelow in which those radicals are present).

A bridging hydroxy-protecting group (especially one formed by $R_a'$ and $R_c'$) is preferably selected from methylene, ethylidene, tert-butylmethylidene, 1-tert-butylethylidene, 1phenyl-ethylidene, 1-(4-methoxyphenyl)ethylidene, 2,2,2-trichloroethylidene, vinylmethylidene, cyclopentylidene, cyclohexylidene, cycloheptylidene, benzylidene, p-methoxybenzylidene, 2,4-dimethoxybenzylidene, 3,4-dimethoxybenzylidene, 2-nitrobenzylidene, 4-nitrobenzylidene, mesitylene, phenyl-(1,2-bis(methylenyl)), methoxymethylene, ethoxymethylene, dialkylsilylene, such as tert-butylsilylene, 1,3-(1,1,3,3-tetraisopropyldisiloxanylidene), 1,1,3,3-tetra-tert-butoxydisiloxanylidene, —C(=O)-, ethylboronyl (-($H_3C$—$CH_2$)B—), phenylboronyl (-(phenyl)B—), o-acetamidophenylboronyl or especially isopropylidene.

Carboxy-protecting groups are especially ester-forming, enzymatically and/or chemically removable protecting groups, preferably enzymatically and/or chemically removable protecting groups, such as heptyl, 2-N-(morpholino) ethyl, cholinyl, methoxyethoxyethyl or methoxyethyl; or those which are primarily chemically removable, e.g. alkyl, such as lower alkyl, especially methyl, ethyl, substituted lower alkyl (except for benzyl and substituted benzyl), such as substituted methyl, especially 9-fluorenylmethyl, methoxymethyl, methoxyethoxymethyl, methylthiomethyl, 2-(trimethylsilyl)ethoxymethyl, benzyloxymethyl, pivaloyloxymethyl, methyl, phenylacetoxymethyl, triisopropylsilylmethyl, 1,3-dithianyl-2-methyl, dicyclopropylmethyl, acetonyl, phenacyl, p-bromophenacyl, α-methylphenacyl, p-methoxyphenacyl, desyl, carbamidomethyl, p-azobenzenecarboxamidomethyl, N-phthalimidomethyl or 4-picolyl, 2-substituted ethyl, especially 2-iodo-, 2-bromo- or 2-chloro-ethyl, 2,2,2-trichloroethyl, 2-(trimethylsilyl)ethyl, 2-methylthioethyl, 2-(p-nitrophenylsulfenyl)ethyl, 2-(p- toluenesulfonyl)-ethyl, 2-(2'-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl or 2-cyanoethyl, tert-butyl, 3-methyl-3-pentyl, 2,4-dimethyl-3-pentyl or ω-chloro-lower alkyl, especially 4-chlorobutyl or 5-chloropentyl, cyclopentyl, cyclohexyl, lower alkenyl, especially allyl, methallyl, 2-methylbut-3-en-2-yl, 3-methylbut-2-enyl or 3-buten-1-yl, substituted lower alkenyl, especially 4-(trimethylsilyl)-2-buten-1-yl, cinnamyl or α-methylcinnamyl, lower alkynyl, such as prop-2-ynyl, phenyl, substituted phenyl, especially 2,6-dialkylphenyl, such as 2,6-dimethylphenyl, 2,6-diisopropyl-phenyl, 2,6-di-tert-butyl-4-methylphenyl, 2,6-di-tert-butyl-4-methoxyphenyl, p(methylthio)-phenyl or pentafluorophenyl, benzyl, substituted benzyl, especially triphenylmethyl, diphenylmethyl, bis(o-nitrophenyl)methyl, 9-anthrylmethyl, 2-(9,10-dioxo)anthrylmethyl, 5-dibenzo-suberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, 4-azidomethoxybenzyl, 4-{N-[1-(4,4-dimethyl-2,6-dioxo-cyclohexylidene)-3-methylbutyl]amino}benzyl, piperonyl or p-polymer-benzyl, tetrahydropyranyl, tetrahydrofuranyl, or silyl radicals, such as trilower alkylsilyl, especially trimethylsilyl, triethylsilyl, tert-butyldimethylsilyl, isopropyldimethylsilyl or di-tert-butylmethylsilyl, or phenyl-di-lower alkylsilyl, such as phenyldimethylsilyl; alternatively a carboxy group can also be protected in the form an oxazolyl, 2-alkyl-1,3-oxazolinyl, 4-alkyl-5-oxo-1,3-oxazolidinyl or 2,2-bistrifluoromethyl-4-alkyl-5-oxo-1,3-oxazolidinyl radical.

Amide-protecting groups are especially allyl, tert-butyl, N-methoxy, N-benzoyloxy, N-methylthio, triphenylmethylthio, tert-butyldimethylsilyl, triisopropylsilyl, 4-(methoxymethoxy)phenyl, 2-methoxy-1-naphthyl, 9-fluorenyl, tert-butoxycarbonyl, N-benzyloxycarbonyl, N-methoxy- or N-ethoxy-carbonyl, toluenesulfonyl, N-buten-1-yl, 2-methoxycarbonylvinyl, or especially alkyl, such as lower alkyl, or more especially substituted alkyl, especially benzyl, benzyl substituted by one or more radicals selected from lower alkoxy, such as methoxy, lower alkanoyloxy, such as acetoxy, lower alkylsulfinyl, such as methylsulfinyl, dicyclopropylmethyl, methoxymethyl, methylthiomethyl and N-benzoyloxymethyl; or bis(trimethylsilyl)methyl, trichloroethoxymethyl, tert-butyldimethylsilyloxymethyl, pivaloyloxymethyl, cyanomethyl, benzyl, 4-methoxybenzyl, 2,4-dimethoxybenzyl, 3,4-dimethoxybenzyl, 2-acetoxy4-methoxybenzyl, o-nitrobenzyl, bis(4-methoxyphenyl)phenylmethyl, bis(4-methylsulfinylphenyl)methyl, pyrrolidinomethyl, diethoxymethyl, 1-methoxy-2,2-dimethylpropyl or 2-(4-methylsulfonyl)ethyl.

It is characteristic of protecting groups that they are simple to remove (that is to say without undesirable secondary reactions taking place), for example by solvolysis, reduction, photolysis or alternatively under conditions analogous to physiological conditions, for example enzymatically.

The person skilled in the art will know which protecting groups can be used for which reactions and compounds of the present invention. Hydroxy-protecting groups $R_a$ and $R_a'$ are especially those which can be selectively introduced and removed, more especially those which are not removed during the conversion of compounds of formula XII. Here it is especially advisable to use hydroxy-protecting groups that do not contain too strongly electronegative substituents, more especially lower alkanoyl, such as acetyl, lower alkoxy-lower alkanoyl, such as methoxyacetyl, or protecting groups of the substituted methyl type, especially lower alkoxymethyl, more especially methoxymethyl (MOM), or lower alkoxy-lower alkoxymethyl, especially 2-methoxyethoxymethyl (MEM).

Acyloxy in formula I is especially the radical of an organic carboxylic or sulfonic acid having from 1 to 24 carbon atoms, unsubstituted or substituted by one or more radicals, especially from 1 to 3 radicals, preferably selected from lower alkoxy, halogen, nitro, lower alkoxycarbonyl, phenyl, phenyl-lower alkyl, phenyloxy, lower alkanoyloxy, benzoyloxy, di-lower lower alkyl-amino, N-phenyl-lower alkyl-N-lower alkyl-amino, N,N-di(phenyl-lower alkyl)-amino, carbamoyl, thiocarbamoyl, sulfamoyl and cyano, and saturated or partially or fully unsaturated, and is preferably the radical of an alkanecarboxylic acid or haloalkanecarboxylic acid, especially lower alkanoyl, of an arylcarboxylic acid, especially benzoic acid, or halo-lower alkanesulfonyl, such as trifluoromethanesulfonyl; or, in the case of a compound of formula I, a radical of formula I'

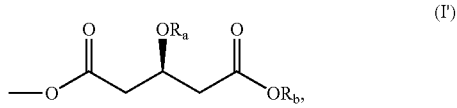

wherein $R_a$ and $R_b$ are as defined for compounds of formula I (the compound of formula I is then a symmetric anhydride (obtainable, for example, by reaction of the acid of formula I (OH instead of X) in the presence of a lower alkanecarboxylic acid anhydride, such as acetic anhydride, in the presence of catalytic amounts of acid)).

Activated hydrocarbyloxy or hydrocarbylthio is preferably unsubstituted or substituted lower alkyloxy, unsubstituted or substituted aryloxy (preferably having from 6 to 12 ring atoms) or unsubstituted or substituted heterocyclyloxy (preferably an unsaturated, fully or partially saturated mono- or bi-cyclic ring system having from 4 to 12 ring atoms and up to three hetero atoms selected from nitrogen, sulfur and oxygen) and is especially lower alkyloxy substituted in the 1-position by esterified carbonyl, such as lower alkoxycarbonyl, cyano or by phenylcarbonyl, especially lower alkoxycarbonylmethoxy, such as ethoxycarbonylmethoxy, cyanomethoxy or phenacyloxy (Ph-CO—CH$_2$—O—), tert-butylthio, N-benzotriazolyloxy, N-succinimidyloxy, pyridyloxy or pyridylthio, especially 2-pyridyloxy or more especially 2-pyridylthio, or electronegatively substituted aryloxy, such as p-nitrophenyloxy, 2,4-dinitrophenyloxy, pentafluorophenyloxy or 2,4,5-trichlorophenyloxy.

"Selectively" means especially enzymatically. In particular, lower alkanoyl, such as acetyl, is removed enzymatically, for example by esterases, such as pig's liver esterase, in suitable buffers, such as phosphate buffer, at preferred pH values of from 5 to 9, especially from 6 to 8. Further possible enzymes and reaction conditions will be found below under the definition of biocatalysts for the hydrolysis. Lower alkoxymethyl, such as MOM, or lower alkoxy-lower alkoxymethyl, such as MEM, is removed by chemical standard methods. The diastereoselective reduction of compound of formula XVIII to form a compound of formula XIX; in each case as defined above and below, is then preferably carried out in a chelate-controlled manner, there being used as chelate-forming agent preferably a di-lower alkyl borinic acid lower alkyl ester, especially diethyl borinic acid ethyl ester. The reduction of the chelated β-hydroxyketone of formula XVIII is then effected with a complex hydride, preferably with an alkali metal borohydride, especially with sodium borohydride. As solvent there are preferably used ethers, such as cyclic ethers, especially tetrahydrofuran, and/or alcohols, such as lower alkanols, e.g. methanol, the preferred reaction temperatures being from −80 to −30° C., especially from −78 to −40° C. In a broader embodiment of the invention it is also possible to use alternative reducing agents, such as sodium cyanoborohydride, but this results in lower diastereoselectivity and is therefore less preferred.

In addition, preferred is the diastereoselective reduction of compound of formula XVIII, wherein $R_b$ is tert.-butyl with hydrogen in the presence of an alkali metal salt or alkaline-earth metal salt and a heterogeneous platinum catalyst to form a syn-diol compound of formula XIX wherein $R_b$ is tert.-butyl. Preferred salt is an alkaline-earth metal salt, most preferred is a magnesium salt, and especially preferred is magnesium acetate. Customary, this diastereoselective reduction is carried under pressure between 1 to 100 bar at temperatures between 0 to 100° C. Most preferably the reduction is carried out using platinum on carbon catalyts together with magnesium acetate with hydrogen under a pressure of 6 to 60 bar at temperatures between 10 to 60° C.

In a broader embodiment of the invention it is also preferred to use alternative reducing agents, such as sodium cyanoborohydride, but this results in lower diastereoselectivity and is therefore less preferred.

The bridging protecting group formed by $R_a'$ and $R_c'$ together, preferably as indicated above, especially the isopropylidene protecting group, is especially introduced by standard methods, preferably as described in the standard works mentioned above, in the case of the isopropylidene protecting group especially by reaction with acetone or, preferably, with a di-lower alkoxypropane, such as dimethoxypropane, in the presence of copper(II) sulfate, zinc chloride or, preferably, an acid, such as sulfuric acid or especially an organic sulfonic acid, such as an arylsulfonic acid (wherein aryl has especially from 6 to 10 ring atoms, e.g. naphthyl or phenyl, and is unsubstituted or mono- or poly-substituted, especially up to tri-substituted, especially by lower alkyl, such as methyl), preferably toluenesulfonic acid, or with a lower alkyl isopropenyl ether, such as ethyl isopropenyl ether, in the presence of an arylsulfonic acid. As preferred solvents there are used aprotic solvents, such as ethers, especially cyclic ethers, more especially tetrahydrofuran, or carboxylic acid amides, such as di-lower alkyl-lower alkanoylamides, e.g. dimethylformamide. The preferred reaction temperatures are in the range of from 0 to 80° C., especially from 20 to 30° C.

The reaction for the preparation of a compound of formula XI to form the corresponding compound of formula I is preferably effected under customary conditions, there being used as reagent for introducing a radical X especially an acid anhydride or an acid halide, preferably an inorganic acid halide, more especially a phosphorus trihalide, phosphorus pentahalide or thionyl halide, such as phosphoryl chloride, phosphoryl bromide, phosphorus trichloride, phosphorus tribromide, phosphorus pentachloride, phosphorus pentabromide, thionyl chloride or thionyl bromide, a symmetric anhydride of a lower alkanesulfonic acid halogenated at the α-carbon atom, such as trifluoromethanesulfonic anhydride, or an acid chloride or a symmetric anhydride of an organic carboxylic acid, especially an oxalyl halide, such as oxalyl chloride or bromide, the reaction being carried out in the absence or preferably presence of a (preferably polar) solvent or solvent mixture, especially in a halogenated hydrocarbon, preferably methylene chloride, in the absence or presence of an acid amide, especially a di-lower alkyl-lower alkanoic acid amide, such as dimethylformamide, at preferred temperatures of from −20° C. to the reflux temperature of the reaction mixture in question, preferably from −10 to 50° C.

Hydrocarbyl $R_d$ in a compound of formula XII is preferably a saturated, fully or partially unsaturated, cyclic (having one or more, especially up to three, fused rings), linear, branched or mixed cyclic-linear or cyclic-branched hydrocarbon radical having up to 24 carbon atoms, preferably up to 10 carbon atoms, especially lower alkyl, and is unsubstituted or mono- or poly-substituted, preferably up to tri-substituted, especially by hydroxy, lower alkoxy, phenyl-lower alkoxy, lower alkanoyloxy, phenyl-lower alkanoyloxy, benzoyloxy, halogen, carboxy, lower alkoxycarbonyl or halo-lower alkyl, such as trifluoromethyl. Preference is given to lower alkyl, especially methyl or more especially ethyl, or lower alkoxy-lower alkyl, especially methoxymethyl. Preferably, in the compounds of formulae XII and XIII the carboxy-protecting group $R_b$ is identical to the hydrocarbyl group $R_d$, especially in each case lower alkyl, more especially methyl or ethyl, branched lower alkyl or lower alkoxy-lower alkyl, especially methoxymethyl.

The preparation of a compound of formula XI is preferably effected with removal of the hydrocarbyl radical $R_d$ in the presence of an enantioselective catalyst, especially a biocatalyst.

As biocatalysts for the hydrolysis there are suitable cells or ruptured cells with the enzymes mentioned below, or especially enzymes as such, preferably esterases, lipases and proteases (peptidases or amidases, see U. T. Bornscheuer and R. T. Kazlauskas, in: Hydrolases in Organic Synthesis, Wiley-VCH, 1999, pages 65–195, ISBN 3-527-30104-6). Common representatives of those classes of enzyme are especially animal esterases (e.g. pig's liver esterase=PLE, pig's pancreas esterase=PPL), esterases from microorganisms or fungi (*B. subtilis esterase, Pichia esterases*yeast *esterases, Rhizopus* sp. esterases (RML, ROL), *Penicillium* sp. esterases, G. candidum (GCL), *H. lanuginosa* (HLL), *Candida* sp. (CAL-A, CAL-B, CCL), *Aspergillus* sp. (ANL), *Pseudomonas* sp. (PCL, PFL) and the like), and also proteases, e.g. subtilisin, thermitase, chymotrypsin, thermolysin, papain, aminoacylases, penicillin amidases, trypsin or the like, to name only a few. The person skilled in the art will be familiar with further suitable enzymes, and the enzymes that can be used are not limited to those mentioned in the above list. Such enzymes can be obtained in the form of crude isolates and/or in purified form from natural sources and/or from recombinant microorganisms by means of modem cloning procedures via overexpression, amplification or the like. Commercially available enzymes are especially preferred. The enzymes can be present as such or immobilised or adsorbed on carriers, for example on silica gel, kieselguhr, such as Celite®, Eupergit® (Röhm & Haas, Darmstadt, Germany) or the like, or used in the form of "CLECs" (cross-linked enzymes), such as are available from ALTUS BIOLOGICS, the scope for use extending beyond the list given, as the person skilled in the art will know (see U. T. Bornscheuer and R. T. Kazlauskas, in: Hydrolases in Organic Synthesis, Wiley-VCH, 1999, pages 61–64, ISBN 3-527-30104-6; K. Faber in: Biotransfornation in Organic Chemistry, Springer 1997, Third Edition, pages 345–357, ISBN 3-540-61688-8; H. J. Rehm, G. Reed in: Biotechnology, VCH 1998, Second Edition, pages 407–411). The enzymes can be used in pure organic solvents, e.g. liquid hydrocarbons, such as hexane, toluene or benzene, liquid ethers, such as diethyl ether, methyl tert-butyl ether or tetrahydrofuran, liquid halogenated hydrocarbons, such as methylene chloride, water or aqueous buffer solutions, in mixtures of those solvents, for example mixtures of one or more thereof with water or aqueous buffer solutions. The aqueous solution is preferably buffered, pH 5–9, it being possible to use customary buffer systems (see e.g. K. Faber in: Biotransformation in Organic Chemistry, Springer 1997, Third Edition, p. 305; or U. T. Bornscheuer and R. T. Kazlauskas, in: Hydrolases in Organic Synthesis, Wiley-VCH, 1999, pages 61–65). The pH is preferably kept substantially constant during the reaction. Most suitable for this purpose is an automatic titrator having a standardised acid or base solution, or manual titration. The reaction temperature is preferably in the range from 10 to 50° C., especially from 25 to 40° C. The amount of biocatalyst used and the concentrations of the reagents can be dependent upon the substrate and the reaction conditions (temperature, solvent etc.) selected in each case, as will be known to the person skilled in the art. There are preferably used commercially available enzymes (for example from Fluka, Sigma, Novo Nordisk, Amano, Roche and the like) or those listed in the current literature (see e.g. H.-J. Rehm, G. Reed in: Biotechnology, VCH 1998, $2^{nd}$ Edition, pages 40–42). Especially preferred for the preparation of enantiomerically pure compounds is α-chymotrypsin in phosphate buffer, especially at pH 7.0.

The preparation of a compound of formula XII from the free hydroxy compound of formula XIII is effected with introduction of a hydroxy-protecting group, reagents that introduce suitable hydroxy-protecting groups being known, preferably as described in the mentioned standard works relating to protecting groups. The introduction of a lower alkanoyl or lower alkoxy-lower alkanoyl is preferably carried out with a corresponding anhydride, especially a lower alkanoyl anhydride, such as acetic anhydride, or a corresponding acid halide, such as a lower alkoxy-lower alkanoyl halide, such as methoxyacetyl chloride, in the presence of a nitrogen base, especially pyridine, in the presence or absence of an inert solvent, especially a halogenated hydrocarbon, such as methylene chloride, at preferred temperatures of from −20 to 50° C., especially from −10 to 30° C.

The preparation of an amide of formula I* from a compound of formula I is carried out under customary conditions for the introduction of ammonia or amines and, where applicable, amide-protecting groups. For example, for the introduction of —NH$_2$(R*=R**=H) reaction with ammonia is carried out, preferably in a suitable solvent, such as an ether, e.g. a di-lower alkyl ether, such as tert-butyl methyl ether, at preferred temperatures of from −20 to 30° C., e.g. at 0° C. For the introduction of substituted alkyl radicals (especially R*=R**=benzyl), reaction with the corresponding amine (e.g. dibenzylamine) is carried out in the presence of a tertiary nitrogen base, such as a tri-lower alkylamine or pyridine, dimethylaminopyridine or the like, in a suitable solvent, such as a halogenated hydrocarbon, e.g. methylene chloride, at preferred temperatures of from −20 to 3020 C., especially at approximately 0° C.

The dehydration of a compound of formula I* wherein R* and R** are each, hydrogen, R$_b$' is a carboxy-protecting group and R$_c$' is a hydroxy-protecting group to form a compound of formula (XVII) is carried out in the presence of suitable dehydrating agents, such as phosphorus(V) oxide or phosphoryl chloride at elevated temperatures, or with cyanuric chloride, in an aprotic solvent, especially an ether, such as a lower alkane-lower alkyl ether, e.g. tert-butyl methyl ether, and/or an acid amide, especially an N,N-di-lower alkyl-lower alkanoylamide, such as dimethylformamide, at preferred temperatures of from 10° C. to the reflux temperature, for example from 20 to 30° C.

The reduction of a cyano compound of formula XIX to form an amino compound of formula VI is carried out under customary conditions, especially by catalytic hydrogenation in the presence of transition metal catalysts, such as Raney nickel, optionally doped e.g. with molybdenum, in the presence of ammonia, in a suitable solvent, such as an alcohol, e.g. methanol or ethanol, at preferred temperatures of from 30 to 50° C., especially at about 30° C.

Unless otherwise indicated, halogen is preferably fluorine, chlorine, bromine or iodine, more preferred is chlorine.

Wherever solvents are mentioned hereinabove and hereinbelow it is also possible, where expedient and possible, for mixtures of two or more of the mentioned solvents to be used. The person skilled in the art will know that for certain reactions such solvents or solvent mixtures must be used in anhydrous (absolute) form and that, if necessary, also the reaction vessels used must have dry surfaces.

Where necessary, the said reactions are carried out in the absence of oxygen, and often also in the absence of carbon dioxide and/or atmospheric moisture, for example under protective gas, such as argon or nitrogen.

Where possible, the starting compounds and intermediate compounds can also be used in the form of salts, obtained in the form of salts or converted into salts in accordance with customary processes, for example in the case of carboxy compounds into the corresponding metal salts, such as alkali metal salts, e.g. sodium or potassium salts, or alkaline earth metal. salts, such as calcium salts, or salts with nitrogen bases, such as ammonium, tri-lower alkyl-ammonium, pyridinium salts or the like. Where salt formation is possible, any reference to any of the compounds should be understood as also including the corresponding salts.

In addition to the solvents already mentioned, it is also possible to use other suitable solvents, where expedient and possible for the reaction in question. Such solvents can be selected, for example, from the following list water, esters, e.g. lower alkyl-lower alkanoates, such as diethyl acetate, ethers, e.g. aliphatic ethers, such as diethyl ether, or cyclic ethers, such as dioxane or tetrahydrofuran, liquid aromatic hydrocarbons, such as benzene or toluene, alcohols, such as methanol, ethanol or 1- or 2-propanol, nitriles, such as aceto-nitrile, halogenated hydrocarbons, such as dichloromethane, chloroform or ethylene chloride, acid amides, such as dimethylformamide, bases, e.g. heterocyclic nitrogen bases, such as pyridine, carboxylic acids, such as lower alkanecarboxylic acids, e.g. acetic acid, carboxylic acid anhydrides, e.g. lower alkanoic acid anhydrides, e.g. acetic anhydride, cyclic, linear or branched hydrocarbons, such as cyclohexane, hexane or isopentane, or mixtures of such solvents or other solvents, e.g. aqueous solutions. Such solvents and solvent mixtures can also be used in working-up, e.g. by chromatography or partition. Any mention of solvents or eluants hereinabove and hereinbelow should be understood as including also mixtures of such solvents or eluants.

PREFERRED EMBODIMENTS OF THE INVENTION

Preferred aspects of the invention can be found in the claims, which are incorporated herein by reference.

Hereinabove and hereinbelow, the radicals in compounds of the formulae of the present invention have the meanings given hereinabove and hereinbelow (especially the specific meanings mentioned for certain reaction variants or methods), and the reaction conditions are in each case as defined hereinabove or hereinbelow, preferably as the preferred reaction conditions:

Preference is given to a process for the preparation of statin derivatives which comprises the preparation of a compound of formula I, as defined hereinabove and hereinbelow, from a compound of formula XI, preferably such a process for the preparation of a compound of formula I; the compound of formula XI in turn preferably being prepared from a compound of formula XII which, in turn, is preferably prepared from a compound of formula XIII.

Preference is given to a process for the preparation of statin derivatives, especially of formula VI, comprising initially the conversion of the compound of formula I into a compound of formula I*; then preferably conversion of a compound of formula I* wherein R* and R** are hydrogen, with dehydration, into a compound of formula XVII, then lengthening thereof to form a nitrile of formula XVIII, conversion thereof into a syn-diol XIX and reduction thereof to form a compound of formula VI.

In all the preferred embodiments, if necessary one or more or all of the protecting groups present are removed or one or more or all of the functional groups that are not to participate in a reaction, or that would interfere with the reaction, are converted into protected groups by the introduction of suitable protecting groups (especially hydroxy-protecting groups and/or carboxy-protecting groups); and, where salt-forming groups are present and the reaction in question is not impaired, the compounds of the present invention may also be in salt form.

A further embodiment of the present invention concerns the use of the compounds and processes of any of the preceeding claims for the preparation of a compound of formula VI.

In addition, the present invention relates to the use of a compound of formula VI for the preparation of Atorvastatin®. Atorvastatin® is commercially available, such as from Warner-Lambert/Gödecke-Parke Davies/Pfizer.

Of the compounds, the invention relates especially to those of formulae I, I*, VI, XVIII and XIX as such, especially those in which the substituents correspond to the radicals indicated in the respective Examples.

Special preference is given to the compounds 1d, 1e, and Bb mentioned in the Examples, especially each individual compound.

The present invention relates especially to the reaction steps and new intermediate compounds mentioned in the following Examples.

EXAMPLES

The following Examples serve to illustrate the invention but do not limit the scope thereof.

Abbreviations Used:
Celite Celite®, filtration aid based on kieselguhr, trade mark of Celite Corp., USA
TLC thin-layer chromatography
DMF dimethylformamide
eq. equivalent
h hour(s)
Hünig's base N-ethyldiisopropylamine
min minute(s)
NMR nuclear magnetic resonance spectroscopy
PLE pig's liver esterase
m.p. melting point (° C.)
THF tetrahydrofuran torr unit of pressure (mm mercury column); 1 torr corresponds to 0.1333 kPa Unless otherwise indicated, the ratios of the components of eluant mixtures, solvent mixtures and the like are given in parts by volume (v/v).

Reaction scheme I for Examples 1 to 4:

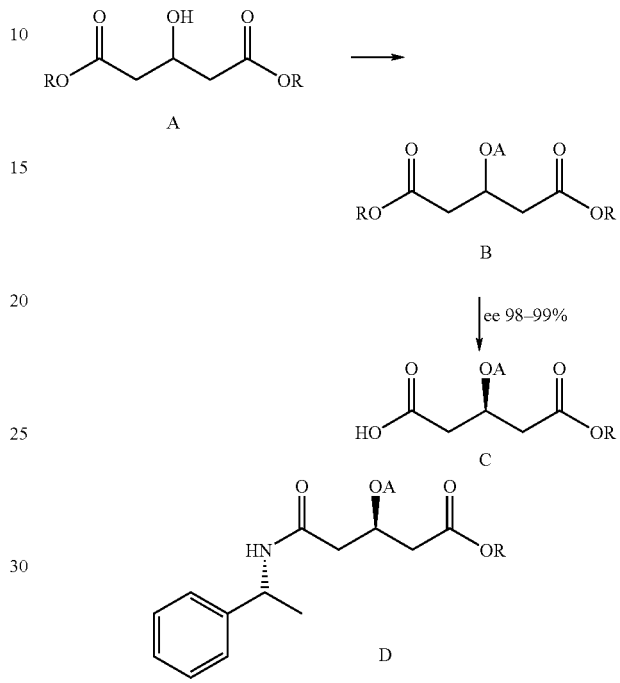

a: A = C(O)CH$_3$
b: A = C(O)CH$_2$OCH$_3$
c: A = CH$_2$OCH$_3$
d: A = CH$_2$OCH$_2$CH$_2$OCH$_3$
R = CH$_2$CH$_3$

Example 1 a) Precursor of formula Ba wherein R=ethyl, A=acetyl (diethyl-3-acetoxyglutaric acid):

54.0 g of diethyl-3-hydroxyglutaric acid (Fluka, Buchs, Switzerland) are dissolved at room temperature in 26.5 ml of pyridine and 27.4 ml of acetic anhydride and the mixture is stirred for about 12 h until all the starting material has reacted. The mixture is diluted with ethyl acetate and washed in succession with water, 1N hydrochloric acid, saturated sodium hydrogen carbonate solution and saturated sodium chloride solution. The organic phase is separated and dried over magnesium sulfate. After evaporation of the organic solvent, 64.3 g of NMR-spectroscopically pure acetate, the title compound, remain: $^1$H-NMR (CDCl$_3$): 1.24 (t, 6H); 2.01 (s, 3H); 2.69 (d, 4H); 4.14 (q, 4H); 5.50 (quin., 1H).

b) Compound of formula Ca wherein R=ethyl, A=acetyl (monoethyl-3(R)-acetoxyglutaric acid):

160 g of diethyl-3-acetoxyglutaric acid Ba are suspended at room temperature in 570 ml of distilled water, and 168 ml of 0.1M phosphate buffer (pH 7) are added. After the addition of 2.7 g of α-chymotrypsin (Sigma, Sigma Chemie, Buchs, Switzerland), the mixture is stirred vigorously and maintained at pH 7.8 using a pH meter and pH stat (Metrohm) and 0.5N sodium hydroxide solution. When the theoretical amount of hydroxide solution (1.3 litres) has been consumed, the mixture is extracted with ethyl acetate. The aqueous phase is adjusted to pH 1 with concentrated hydrochloric acid (conc. HCl) and then extracted with ethyl acetate. Any cloudiness of the organic phase can be removed by filtration over Celite. After evaporation of the organic phase, 131 g (97%) of semi-ester Ca remain: $^1$H-NMR (CDCl$_3$): 1.25 (t, 3H); 2.03 (s, 3H); 2.71 (d, 2H); 2.77 (d, 2H); 4.14 (q, 2H); 5.50 (quin., 1H).

Determination of the enantiomeric excess (ee) of the monoacid Ca by means of the amide Da (R=ethyl, A=acetyl):

150 mg of the monoacid Ca are reacted in accordance with the customary methods of peptide coupling with 341 mg of (benzotriazol-1-yloxy)-tris(dimethylamino)phosphonium hexafluorophosphate, 246 mg of Hünig's base and 93 µl of R-phenylethylamine (Fluka, Buchs, Switzerland) in 1.5 ml of DMF at room temperature. After customary extraction, 188 mg of amide Da are obtained. NMR spectroscopy indicates a diastereoisomeric ratio of 99:1 on the basis of the shift difference between the two diastereoisomeric acetates and accordingly a ratio of R to S of 99:1. HPLC analysis (column: Chiracel OJ 25 cm×0.46 cm (Daicel Chemical Industries, Ltd., JP), n-hexane:ethanol=95:5, flow rate 1.2 ml/min, UV detection at 210 nm) confirms the ratio of R to S as 98.8:1.2. $^1$H-NMR (CDCl$_3$): 1.15 (t, 3H); 1.35 (d, 3H); 1.85 and 1.87 (2×s, total 3H, ratio as 99:1); 2.47 (m, 2H); 2.55 (dd, 1H); 2.65 (d, 1H); 4.01 (broad q, 1H); 5.00 (quint., 1H); 5.38 (m, 1H); 6.51 (broad d, NH); 7.20 (m, 5H).

Example 2 a) Precursor of formula Bb wherein R=ethyl, A=methoxyacetyl (diethyl-3-methoxy-acetoxyglutaric acid):

50.0 g of diethyl-3-hydroxyglutaric acid (Fluka, Buchs, Switzerland) are dissolved at 0° C. in 80 ml of dichloromethane; 20.6 ml of pyridine and 22.9 ml of methoxyacetyl chloride are added and the mixture is stirred at room temperature for about 12 h until all the starting material has reacted. The mixture is washed in succession with water, 1N hydrochloric acid, saturated sodium hydrogen carbonate solution and saturated sodium chloride solution. The organic phase is separated and dried over magnesium sulfate. After evaporation of the organic solvent, a dark-yellow syrup is obtained which is filtered over a small amount of silica gel using hexane/ethyl acetate (2:1). After evaporation of the solvent, 65.0 g of NMR-spectroscopically pure methoxyacetate Bb are obtained: $^1$H-NMR (CDCl$_3$): 1.20 (t, 3H); 2.65 (d, 4H); 3.35 (s, 3H); 3.90 (s, 2H); 4.04 (q, 4H); 5.55 (quin., 1H).

b) Compound of formula Cb wherein R=ethyl, A=methoxyacetyl (monoethyl-3(R)-methoxyacetoxyglutaric acid):

40.0 g of diethyl-3-methoxyacetoxyglutaric acid Bb are suspended at room temperature in 150 ml of distilled water, and 43 ml of 0.1M phosphate buffer (pH 7) are added. After the addition of 0.4 g of α-chymotrypsin (Sigma; Sigma Chemie, Buchs, Switzerland), the mixture is stirred vigorously and maintained at pH 7.8 using a pH meter and pH stat (Metrohm) and 0.5N sodium hydroxide solution. After 18 h, a further 0.1 g of chymotrypsin is added and stirring is continued until the theoretical amount of hydroxide solution has been consumed. The mixture is then extracted with ethyl acetate (4×). The aqueous phase is adjusted to pH 1 with concentrated hydrochloric acid (conc. HCl) and then extracted with ethyl acetate. Any cloudiness of the organic phase can be removed by filtration over Celite. After evaporation of the organic phase, 24.8 g of semi-ester Cb remain: $^1$H-NMR (CDCl$_3$): 1.24 (t, 3H); 2.74 (d, 2H); 2.75 (d, 2H); 3.42 (s, 3H); 3.99 (s, 2H); 4.14 (q, 2H); 5.59 (quin., 1H).

Alternatively, immobilised chymotrypsin can also advantageously be used. It can be supported on silica gel (Sigma S0507, 230–400 mesh, average pore diameter 0.6 nm; Sigma Chemie, Buchs, Switzerland) by customary methods without loss of activity, easily removed and then used repeatedly.

c) Determination of the enantiomeric excess (ee) of the monoacid Cb by means of benzamide Db (R=ethyl, A=methoxyacetyl):

200 mg of the monoacid Cb are reacted by customary methods of peptide coupling with 392 mg of (benzotriazol-1-yloxy)-tris(dimethylamino)phosphonium hexafluorophosphate, 290 µl of Hünig's base and 88 µl of benzylamine (Fluka, Buchs, Switzerland) in 2.0 ml of DMF at room temperature. After customary extraction, 178 mg of amide Db are obtained. HPLC analysis (Chiracel OD 25 cm×0.46 cm (Daicel Chemical Industries, Ltd., JP), n-hexane:ethanol=9:1, flow rate 1 ml/min, UV detection at 210 nm) yields a ratio of R to S of 98.6:1.4. $^1$H-NMR (CDCl$_3$): 1.22 (t, I=7.0, 3H); 2.62 (d, I=6.5, 2H); 2.75 (dd, I=15.8, 5.3, 2H); 3.35 (s, 3H); 3.91 (s, 2H); 4.10 (q, I=7.0, 2H); 4.38 (d, I=5.9, 2H); 5.56–5.65 (m, 1H); 6.31 (t, br, NH); 7.21–7.33 (m, 5H).

d) Purification of the compound Cb wherein R=ethyl, A=methoxyacetyl (monoethyl-3(R)-methoxyacetoxyglutaric acid):

500 g of monoacid Cb are dissolved in 2 litres of tert-butyl methyl ether and heated to boiling. 400 ml (1 eq.) of dicydohexylamine dissolved in 2 litres of tert-butyl methyl ether are added dropwise in the course of 10 min, followed by 4 litres of n-hexane. If crystallisation does not start spontaneously, seeding is carried out, followed by cooling to 5–10$_{20}$ C. The resulting crystals are filtered off with suction and dried in vacuo at 70° C. Yield: 694 g, 80% white crystals, m.p.=111° C. 3 g of the resulting salt are dissolved in 20 ml of water, NaCl is added to the solution and 1 eq. of 3N hydrochloric acid is added. The precipitated dicyclohexylamine hydrochloride is filtered off with suction and the clear filtrate is extracted repeatedly with tert-butyl methyl ether. After drying and removal of the solvent, 1.6 g, 92%, of monoacid Cb are obtained; ee≧99.5%, determined by way of the benzamide analogously to c).

Example 3 a) Precursor of formula Bc wherein R=ethyl, A=methoxymethyl (diethyl-3-methoxymethoxyglutaric acid):

97.2 g of diethyl-3-hydroxyglutaric acid A (Fluka) are dissolved at 0° C. together with 210 ml of formaldehyde dimethylacetal in 350 ml of dichloromethane, and 61.3 g of phosphorus pentoxide are added in portions. The mixture is stirred vigorously overnight, the temperature of the mixture rising to room temperature. When conversion is complete (TLC monitoring), the mixture is decanted off, diluted with methylene chloride and washed in succession with 2×saturated sodium hydrogen carbonate solution and saturated sodium chloride solution. The organic phase is separated and dried over magnesium sulfate. After evaporation of the solvent, a colourless fluid is obtained which is distilled at 98–101° C./0.17 torr. 104.8 g (89%) of a colourless fluid, the title compound, are obtained: $^1$H-NMR (CDCl$_3$): 1.15 (t, 3H); 2.53 (m, 4H); 3.24 (s, 3H); 4.05 (q, 4H); 4.30 (quin., 1H); 4.58 (s, 2H).

b) Compound of formula Cc wherein R=ethyl, A=methoxymethyl (monoethyl-3(R)-methoxymethoxyglutaric acid):

7.4 g of diethyl-3-methoxymethoxyglutaric acid Bc are suspended at room temperature in 100 ml of distilled water, and 20 ml of 0.1M phosphate buffer (pH 7) are added. After the addition of 1.0 g of chymotrypsin, the mixture is stirred vigorously and maintained at pH 7.8 using a pH meter and pH stat (Metrohm) and 0.5N sodium hydrogen carbonate solution. When the theoretical amount of carbonate solution has been consumed, the mixture is extracted with ethyl acetate. The aqueous phase is adjusted to pH 3–3.5 with 0.5N hydrochloric acid and then extracted with ethyl acetate. Any cloudiness of the organic phase can be removed by filtration over Celite. After washing of the organic phase with saturated sodium chloride solution and evaporation of the organic phase, 5.4 g (82%) of spectroscopically clean monoacid, the title compound, remain: $^1$H-NMR (CDCl$_3$): 1.24 (t, 3H); 2.69 (m, 4H); 3.34 (s, 3H); 4.13 (q, 2H); 4.38 (quin., 1H); 4.68 (s, 2H).

c) Determination of the enantiomeric excess (ee) of the monoacid Cc by means of the amide with benzylamine:

400 mg of the monoacid are reacted by customary methods for peptide coupling with 760 mg of (benzotriazolyl-1-yloxy)-tris(dimethylamino)phosphonium hexafluorophosphate, 215 µl of Hünig's base and 0.70 ml of benzylamine (Fluka) in 2.0 ml of DMF at from 0° C. to room temperature. After customary extraction, 567 mg of amide are obtained. HPLC analysis (Chiralcel OD, 25×0.46 cm, n-hexane:ethanol=98:2, 1 ml/min) confirms a ratio of R to S of more than 98:2. $^1$H-NMR (CDCl$_3$): 1.19 (t, 3H), 2.48 (dd, 2H); 2.56 (dd, 1H); 3.24 (s, 2H); 4.06 (broad q, 1H); 4.34 (m, 3H); 4.59 (m, 2H); 7.00 (broad s, NH); 7.20 (m, 5H).

Example 4 a) Precursor of formula Bd wherein R=ethyl, A=2-methoxyethoxymethyl (diethyl-3-(2-methoxyethyl)-oxymethoxyglutaric acid):

At 0° C., 11.23 g of diethyl-3-hydroxyglutaric acid A (Fluka) are introduced together with 11.8 ml of diisopropylethylamine into 40 ml of dichloromethane, and 8.6 g of 2-methoxy-ethoxymethyl chloride (Fluka) are added. The mixture is stirred vigorously overnight, the temperature of the mixture rising to room temperature. The mixture is diluted with methylene chloride and washed in succession with 2×1N hydrochloric acid, 2×saturated sodium hydrogen carbonate solution and saturated sodium chloride solution. The organic phase is separated and dried over magnesium sulfate. After evaporation of the solvent, a colourless liquid is obtained, 15.91 g (99%), the title compound. $^1$H-NMR (CDCl$_3$): 1.20 (t, 3H); 2.59 (m, 4H); 3.32 (s, 3H); 3.49 (m, 2H); 3.63 (m, 2H); 4.09 (q, 4H); 4.36 (quin., 1H); 4.73 (s, 2H).

b) Compound of formula Cd wherein R=ethyl, A=2-methoxyethoxymethyl (monoethyl-3(R)-(2-methoxyethyl)-oxymethoxyglutaric acid):

7.4 g of diethyl-3-(2-methoxyethyl)-oxymethoxyglutaric acid Bd are suspended at room temperature in 30 ml of distilled water, and 3.3 ml of 0.1M phosphate buffer (pH 7) are added. After the addition of 0.1 g of chymotrypsin, the mixture is stirred vigorously and maintained at pH 7.8 using a pH meter and pH stat (Metrohm) and 0.5N sodium hydroxide solution. When the theoretical amount of hydroxide solution has been consumed, the mixture is extracted with ethyl acetate. The aqueous phase is adjusted to pH 3–3.5 with 0.5N hydrochloric acid and then extracted with ethyl acetate. Any cloudiness of the organic phase can be removed by filtration over Celite. After washing of the organic phase with saturated sodium chloride solution and evaporation of the organic phase, 1.44 g (79%) of spectroscopically clean monoacid, the title compound, remain: $^1$H-NMR (CDCl$_3$): 1.25 (t, 3H); 2.02 (s, 3H); 2.67 (m, 4H); 3.38 (s, 3H); 3.55 (m, 2H); 3.69 (m, 2H); 4.12 (q, 4H); 4.41 (quin., 1H); 4.79 (q, 2H).

c) Determination of the enantiomeric excess (ee) of the monoacid Cc by means of the amide Dc ((R=ethyl, A=2-methoxyethoxymethyl):

380 mg of the monoacid Cd are reacted in accordance with customary methods for peptide coupling with 682 mg of (benzotriazolyl-1-yloxy)-tris(dimethylamino)phosphonium hexaflurophosphate, 493 µl of Hünig's base and 185 µl of R-phenylethylamine (Fluka) in 3.0 ml of DMF at from 0° C. to room temperature. After customary extraction, 403 mg of amide are obtained. NMR-spectroscopy indicates a diastereoisomeric ratio of greater than 95:5 on the basis of the shift difference between the two methoxy groups in the diastereoisomers. HPLC analysis (Chiralcel OD, 25×0.46 cm, n-hexane:ethanol=95:5, 1 ml/min) confirms the ratio of R to S as 98:2. $^1$H-NMR (CDCl$_3$): 1.22 (t, 3H); 1.45 (d, 3H); 2.48 (m, 2H); 2.62 (m, 2H); 3.30 (s, ca. 5%); 3.38 (s, 95%); 3.50 (m, 4H); 4.12 (1, 1H); 4.34 (quint., 1H); 4.79 (q, 2H); 5.11 (quint, 1H); 6.54 (broad d, NH); 7.34 (m, 5H).

Reaction scheme II for Examples 5, 6 and 8 (the radicals being as defined in the Examples):

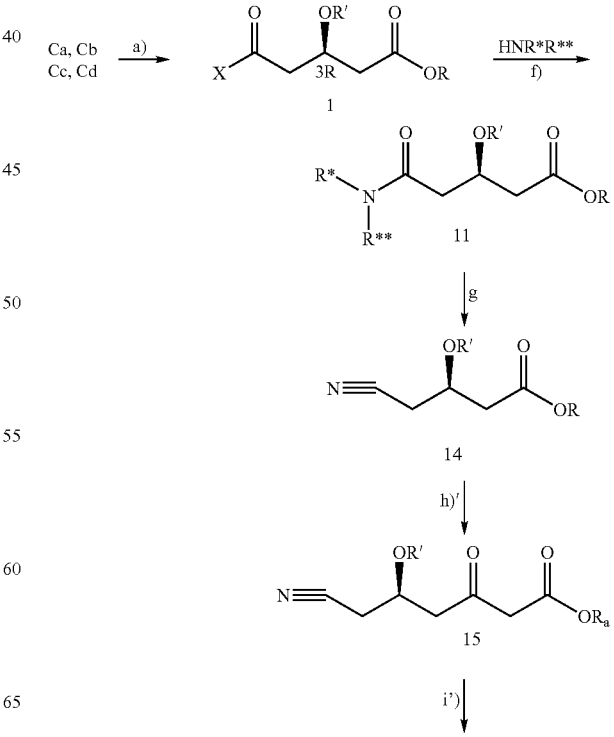

-continued

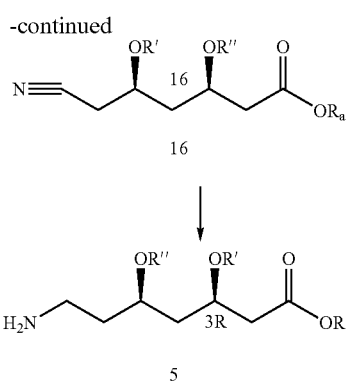

Example 5

Glutaric Acid Semihalides of Formula 1 a) Monoethyl ester of (3R)-acetoxy-glutaric acid chloride 1a (R=ethyl, X=Cl, R'=acetyl):

30.0 g of (3R)-acetoxyglutaric acid monoethyl ester (Ca) are dissolved in 60 ml of dry dichloromethane to which 20 drops of dry DMF have been added, and at 0–5° C. the solution is slowly treated with 21.9 g of oxalyl chloride. The mixture is then stirred for about 30 min. at 0° C. and then for a further 1.5 h at room temperature until the evolution of gas can no longer be observed. After evaporation of the solvent, 32.6 g of NMR-spectroscopically pure acid chloride 1a remain. (Colourless product can be obtained after molecular distillation). $^1$H-NMR CDCl$_3$): 1.25 (t, 3H); 2.04 (s, 3H); 2.66 (dd, 1H); 2.70 (dd, 1H); 3.30 (dd, 1H); 3.34 (dd, 1H); 4.16 (q, 2H); 5.47 (m, 1H).

b) Monoethyl ester of (3R)-acetoxyglutaric acid bromide 1b (R=ethyl, X=Br, R'=acetyl):

5.0 g of (3R)-acetoxyglutaric acid monoethyl ester (Ca) are dissolved in 18 ml of dry dichloromethane to which a drop of dry DMF has been added, and at 0–50° C. the solution is slowly treated with 6.7 g of oxalyl bromide. The mixture is then stirred for about 30 min. at 0° C. and then for a further 2 h at room temperature until the evolution of gas can no longer be observed. After evaporation of the solvent, 6.6 g (98%) of spectroscopically pure acid bromide 1b remain: $^1$H-NMR (CDCl$_3$): 1.21 (t, 3H); 2.00 (s, 3H); 2.62 (dd, 1H); 3.39 (dd, 1H); 3.42 (dd, 1H); 4.11 (q, 2H); 5.41 (m, 1H).

c) Monoethyl ester of (3R)-methoxyacetoxyglutaric acid chloride 1c (R=ethyl, X=Cl, R'=methoxyacetyl):

21.0 g of monoethyl-3(R)-methoxyacetoxyglutaric acid Cb are dissolved in 100 ml of dry dichloromethane to which 40 µl of dry DMF has been added, and at 0–5° C. the solution is slowly treated with 13.9 g of oxalyl chloride. The mixture is then stirred for about 4 h, the temperature of the mixture rising to room temperature. The mixture is then diluted with ethyl acetate and extracted 3×with icewater, and the organic phase is dried over sodium sulfate. After evaporation of the solvent, 20.9 g of NMR-spectroscopically pure acid chloride 1c remain: $^1$H-NMR (CDCl$_3$): 1.20 (t, 3H); 2.04 (s, 3H); 2.67 (m, 2H); 3.32 (m, 2H); 3.36 (s, 3H); 3.95 (s, 2H); 4.09 (q, 2H); 5.52 (m, 1H).

d) Monoethyl ester of (3R)-methoxymethoxyglutaric acid chloride 1d (R=ethyl, X=Cl, R'=methoxymethyl):

0.40 g of the monoacid Cc is dissolved in 2 ml of dry dichloromethane to which 3 drops of dry DMF are added, and at 0–5° C. the solution is slowly treated with 0.18 ml of oxalyl chloride until the evolution of gas can no longer be observed. After evaporation of the solvent, 0.43 g of acid chloride 1d remains: $^1$H-NMR (CDCl$_3$): 1.25 (t, 3H); 2.67 (m, 4H); 3.69 (s, 3H); 4.13 (q, 2H); 5.53 (q, 1H); 5.54 (s, 2H).

e) Monoethyl ester of (3R)-(2-methoxyethyl)-oxymethoxy-glutaric acid chloride 1e (R=ethyl, X=Cl, R'=2-methoxy-ethyloxymethyl):

0.53 g of the monoacid Cd is dissolved in 2 ml of dry dichloromethane to which 2 drops of dry DMF have been added, and at 0–5° C. the solution is slowly treated with 0.21 ml of oxalyl chloride until the evolution of gas can no longer be observed. After evaporation of the solvent, 0.54 g of acid chloride 1e remains: $^1$H-NMR (CDCl$_3$): 1.21 (t, 3H); 2.55 (m, 1H); 2.65 (m, 1H); 3.24 (m, 2H); 3.34 (s, 3H); 3.50 (m, 2H); 3.65 (m, 2H); 4.10 (q, 2H); 4.38 (quint., 1H); 4.74 (m, 2H).

Example 6

Preparation of Compounds 11, 14, 15, 16 and 5'

(i) (f) Preparation of 11a (R=ethyl, R'=acetyl, R*=H, R**=H)

50 g of (3R)-acetoxyglutaric acid monomethyl ester monochloride 1a are dissolved in 500 ml of tert-butyl methyl ether and at 0° C. treated with ammonia gas until the absorption of ammonia has ceased. The precipitated ammonium chloride is filtered off. After evaporation of the solvent, 44.5 g (97%) of NMR-spectroscopically pure amide 11a remain: $^1$H-NMR (CDCl$_3$): 1.24 (t, 3H); 2.02 (s, 3H); 2.60 (dd, 2H); 2.72 (m, 2H); 4.13 (q, 2H); 5.47 (m, 1H); 5.95 (s, br, 2H).

(ii) (f) Preparation of 11b (R=ethyl, R=acetyl, R*=benzyl, R**=benzyl)

At 0° C., a mixture of 41.7 g of dibenzylamine and 21.4 g of triethylamine is slowly added dropwise to 50 g of (3R)-acetoxyglutaric acid monomethyl ester monochloride 1a in 250 ml of methylene chloride and the mixture is stirred at room temperature for a further 2 h. The reaction mixture is then washed with 100 ml of 0.1N HCl and 2×100 ml of water and the organic phase is dried over sodium sulfate. After evaporation of the solvent, 79.8 g (95%) of NMR-spectroscopically pure dibenzylamide 2b remain: $^1$H-NMR (CDCl$_3$): 1.24 (t, 3H); 1.99 (s, 3H); 2.72 (m, 2H), 2.90 (m, 2H); 4.13 (qq, 2H); 4.48 (q, 2H); 4.55 (q, 2H), 5.63 (m, 1H), 7.25 (m, 10H).

(iii) (f) Preparation of 11c (R=ethyl, R=H, R*=benzyl, R**=benzyl)

60 g of (3R)-acetoxyglutaric acid monoethyl ester mono (N,N-dibenzyl)amide 11b are stirred in 600 ml of 2M ethanolic HCl at room temperature for 12 h. After evaporation of the solvent, 53.1 g (99%) of NMR-spectroscopically pure dibenzylamide 11c remain: $^1$H-NMR (CDCl$_3$): 1.24 (t, 3H); 2.60 (m, 2H); 2.90 (m, 2H); 4.10 (q, 2H); 4.43 (m, 2H), 4.50 (m, 1H); 4.55 (m, 2H), 7.25 (m, 10H).

(iv) (g') Preparation of 14a (R=ethyl, R'=acetyl)

A solution of 100 g of (3R)-acetoxyglutaric acid mono-ethyl ester monoamide 11a in 500 ml of tert-butyl methyl ether and 180 ml of dimethylformamide is mixed with 30 g of cyanuric chloride dissolved in 500 ml of tert-butyl methyl ether, and stirred at room temperature for 2 h. The precipitated cyanuric add is filtered off and the organic solution is washed with 500 ml of saturated sodium hydrogen carbonate solution. The aqueous phase is re-extracted with w×300 ml of tert-butyl methyl ether and the combined organic phases are washed with 2×500 ml of water. The organic phase is dried over sodium sulfate. After evaporation of the solvent, 82.5 g (90%) of NMR-spectroscopically pure nitrile 14a remain: $^1$H-NMR (CDCl$_3$): 1.24 (t, 3H); 2.07 (s, 3H); 2.74 (m, 2H); 2.82 (m, 2H); 4.13 (q, 2H); 5.29 (m, 1H).

(v) (Conversion according to g') Preparation of 14b (R=ethyl, R'=H):

60 g of 14a are stirred in 600 ml of 2M ethanolic HCl for 12 h at room temperature. After evaporation of the solvent, the residue is taken up in 500 ml of ethyl acetate and washed with 200 ml of saturated sodium hydrogen carbonate solution and 2×200 ml of water. The organic phase is dried over sodium sulfate and the solvent is evaporated off. After distillation of the residue (0.03 mbar, 103–105° C.), 41.6 g (88%) of NMR-spectroscopically pure nitrile 14b are obtained as a single fraction: $^1$H-NMR (CDCl$_3$) 1.20 (t, 3H); 2.55 (m, 4H); 3.80 (s, br, 1H); 4.27 (q, 2H).

(vi) (h') Preparation of 15a (Ra=tert-butyl, R'=H)

Starting from 14b, the known compound 15a is prepared by known processes (see Brower, P., et al., Tetrahedron Lett. 33(17), 2279–2282 (1992)) by reaction with lithio-tert-butyl acetate in hexane/THF.

(vii) (i') Preparation of 16a (Ra=tert-butyl, R'=H, R"=H)

Starting from 15a, the known syn-diol 16a is prepared by known processes (see Brower, P., et al., Tetrahedron Lett. 33(17), 2279–2282 (1992)) by diastereoselective reduction in the presence of NaBH$_4$/B(CH$_2$CH$_3$)$_2$OCH$_3$.

(viii) (Conversion according to i' or I") Preparation of 16b (Ra=tert-butyl, R' and R" together=isopropylidene):

Starting from 15a, the compound 16b is obtained by reaction with acetone dimethyl ketal by known processes (see Brower, P., et al, Tetrahedron Lett. 33(17), 2279–2282 (1992)).

Example 7

Further Use of Compound 5 from Reaction Scheme II

For the preparation of atorvastatin, a compound 5 is reacted with a compound of formula 17

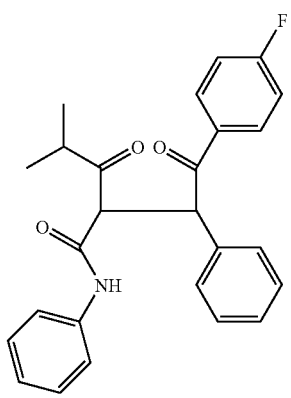

analogously to the conditions described in WO 89/07598 for the reaction between that compound and a compound of formula H$_2$N—CH$_2$CH$_2$—CH(OR$_{10}$)(OR$_{11}$), wherein R$_{10}$ and R$_{11}$ are alkyl having up to 8 carbon atoms or together are 1,2-(1-methyl)ethylidene, 1,2-ethylidene or 1,3-propylidene. Subsequent removal of protecting groups and, if necessary, opening of the lactone ring yields atorvastatin.

Example 8

Syn-selective Hydrogenation of 15 to 16a (Ra=tert-butyl, R'=H, R"=H)

50 mg Pt—C and 50 mg magnesium acetate are placed in a 2.5 ml glass vial. After addition of 100 mg 15 dissolved in 1 ml methanol under argon the vial was placed in a 50 ml autoclave and purged 3 times with hydrogen. The hydrogenation is performed at 20 bar at roomtemperature for 16 hours. The catalyst is removed by filtration and evaporation of the solvent gives 16a in a quantitative yield with a syn/anti ratio of 3.29

What is claimed is:

1. A process for the preparation of the intermediate of formula VI

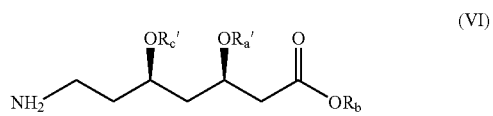

wherein R$_a$' and R$_c$' are each independently of the other hydrogen or a hydroxy-protecting group or together are a bridging hydroxy-protecting group, and R$_b$ is a carboxy-protecting group, which is suitable for the preparation of statin derivatives, which process is carried out by conversion of the intermediate of formula XIX

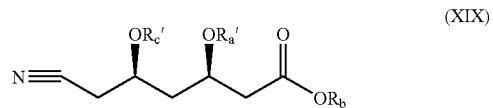

wherein R$_a$' and R$_c$' are each independently of the other hydrogen or a hydroxy-protecting group, and R$_b$ is a carboxy-protecting group; wherein compound of formula XIX is prepared by a process which comprises the preparation of a compound of formula I

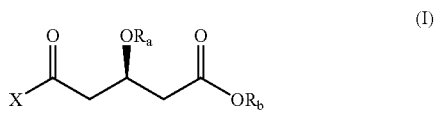

wherein X is halogen, acyloxy, activated hydrocarbyloxy, activated hydrocarbylthio or —N(CH$_3$)—OCH$_3$, R$_a$ is hydrogen or a hydroxy-protecting group and R$_b$ is a carboxy-protecting group; wherein compound of formula I is prepared by conversion of a compound of formula XI

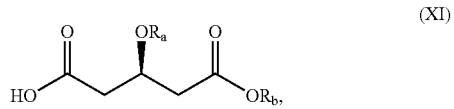

wherein R$_a$ is a hydroxy-protecting group and R$_b$ is a carboxy-protecting group, into the corresponding compound of formula I using a reagent that introduces the radical X.

2. A process according to claim 1, wherein the compound of formula XI is prepared by hydrolysing a compound of formula XII

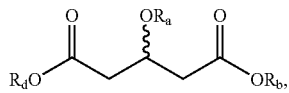
(XII)

wherein $R_a$ is a hydroxy-protecting group, $R_b$ is a carboxy-protecting group and $R_d$ is hydrocarbyl, by means of an enantioselective catalyst, with removal of the radical $R_d$, the corresponding compound of formula XI being obtained directly, the compound of formula XII in turn being obtained by reacting a glutaric acid derivative of formula XIII

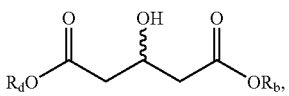
(XIII)

wherein $R_b$ and $R_d$ are as defined for compounds of formula XII, by introduction of a hydroxy-protecting group using the corresponding reagent suitable for the introduction of the protecting group.

3. A process according to claim 1, comprising the conversion of a compound of formula I wherein X is halogen, acyloxy, activated hydrocarbyloxy, activated hydrocarbylthio or —N(CH$_3$)OCH$_3$, $R_a$ is hydrogen or a hydroxy-protecting group and $R_b$ is a carboxy-protecting group into an amide of formula I*

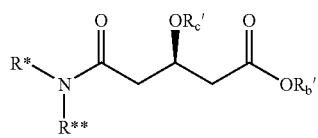
(I*)

wherein $R_c'$ is hydrogen or a hydroxy-protecting group, $R_b'$ is hydrogen or a carboxy-protecting group and R* and R** are each independently of the other hydrogen or an amide-protecting group; which compound I*, wherein R* and R** are each hydrogen, $R_b'$ is a carboxy-protecting group and $R_c'$ is a hydroxy protecting group is dehydrated to form a nitrile of formula XVII

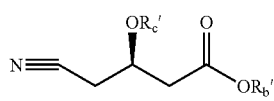
(XVII)

wherein $R_c'$ is a hydroxy-protecting group and $R_b'$, is a carboxy-protecting group; that compound, after removal of the hydroxy-protecting group $R_c'$ is converted by means of a compound of formula XX

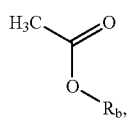
(XX)

wherein $R_b$ is a carboxy-protecting group, in the presence of a strong base, into a nitrile of formula XVIII

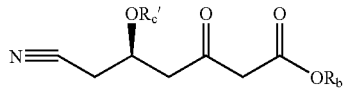
(XVIII)

wherein $R_c'$ is hydrogen and $R_b$ is a carboxy-protecting group; the compound of formula XVIII wherein $R_c'$ is hydrogen is in turn then converted by diastereoselective reduction into a syn-diol compound of formula XIX

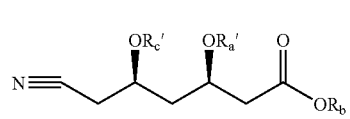
(XIX)

wherein $R_a'$ and $R_c'$ are hydrogen; or, after subsequent introduction of protecting groups, $R_a'$ and $R_c'$ are each independently of the other hydrogen or a hydroxy-protecting group, with the proviso that at least one of the two radicals is such a protecting group, or $R_a'$ and $R_c'$ together are a bridging hydroxy-protecting group; and $R_b$ is a carboxy-protecting group; and by reduction of the cyano function in that compound there is obtained an amino compound of formula VI described in claim 1 wherein $R_a'$ and $R_c'$ are each independently of the other hydrogen or a hydroxy-protecting group or together are a bridging hydroxy-protecting group, and $R_b$ is a carboxy-protecting group.

4. A process according to any of the preceding claims 1 to 3, wherein a compound of formula XVIII

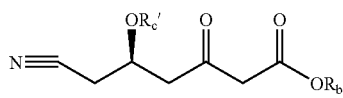
(XVIII)

wherein $R_c'$ is hydrogen and $R_b$ is tert-butyl; is reduced diastereoselectively with hydrogen in the presence of an alkali metal salt or an alkaline-earth metal salt and a heterogeneous platinum catalyst to form a syn-diol compound of formula XIX

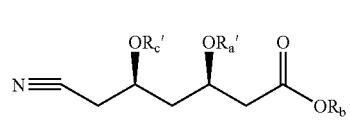
(XIX)

wherein $R_a'$ and $R_c'$ are each independently of the other hydrogen or a hydroxy-protecting group, and $R_b$ is tert-butyl.

5. A process especially according to any of the preceding claims 1 to 3, wherein a compound of formula XVIII, as defined above in claim 3, is reduced diastereoselectively with a mixture of triethylborane or diethylborane methoxide with sodium borhydride to form a syn-diol compound of formula XIX as defined above in claim 3.

6. A process according to claim 2, wherein $R_b$ and $R_d$ are identical.

7. A process according to claim 3, wherein the amide-protecting group is hydroxy alkyl or substituted alkyl.

8. A process according to claim 3, wherein at least one of the compounds of formulae I*, I, VI, XI to XII, or XVII to XIX is present in salt form.

* * * * *

UNITED STATES PATENT AND TRADEMARK OFFICE
CERTIFICATE OF CORRECTION

PATENT NO. : 7,199,261 B2 Page 1 of 2
APPLICATION NO. : 10/481704
DATED : September 10, 2004
INVENTOR(S) : Ohrlein et al.

It is certified that error appears in the above-identified patent and that said Letters Patent is hereby corrected as shown below:

On the Title Page Item (57)

In the Abstract, formula XIX, delete the extra $CH_2$ group on the left, to change Column 6, line 13, change "(imidazolylethyl)carbamoyl]" to
-- (imidazolylethyl)carbamoyl]trityl --

Column 6, lines 59-60, change "pivaloyloxymethyl, methyl, phenylacetoxymethyl," to -- pivaloyloxymethyl, phenylacetoxymethyl, --

Column 8, lines 20-27, change the bond sign on the left of the O to a negative sign, to change

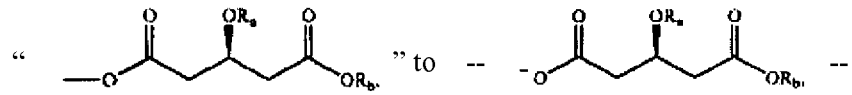

Column 11, line 56, change "3020 C.," to -- 30°C, --

Column 16, line 41, change "5–1020 C." to -- 5–10°C. --

UNITED STATES PATENT AND TRADEMARK OFFICE
CERTIFICATE OF CORRECTION

PATENT NO. : 7,199,261 B2
APPLICATION NO. : 10/481704
DATED : September 10, 2004
INVENTOR(S) : Ohrlein et al.

It is certified that error appears in the above-identified patent and that said Letters Patent is hereby corrected as shown below:

Column 19, line 40, change "0–50° C" to -- 0–5°C --

Column 24, line 52, delete "especially"

Signed and Sealed this

Seventeenth Day of November, 2009

David J. Kappos
*Director of the United States Patent and Trademark Office*